United States Patent [19]

Ishida et al.

[11] 4,320,296

[45] Mar. 16, 1982

[54] METHOD OF AND APPARATUS FOR RECORDING IMAGE PROCESSING DATA IN RADIATION IMAGE RECORDING SYSTEM

[75] Inventors: Masamitsu Ishida; Hisatoyo Kato; Seiji Matsumoto, all of Minami-ashigara, Japan

[73] Assignee: Fuji Photo Film Co., Ltd., Kanagawa, Japan

[21] Appl. No.: 168,803

[22] Filed: Jul. 11, 1980

[30] Foreign Application Priority Data

Jul. 11, 1979 [JP] Japan .................................. 54-87798

[51] Int. Cl.³ ............................................... G03C 5/16
[52] U.S. Cl. .................................................. 250/327.1
[58] Field of Search ............................. 250/327.1, 337

[56] References Cited

U.S. PATENT DOCUMENTS 3,859,527 1/1975 Luckey ................................ 250/337
3,975,637 8/1976 Ikedo et al. ...................... 250/327.1

Primary Examiner—Davis L. Willis
Attorney, Agent, or Firm—Gerald J. Ferguson, Jr.; Joseph J. Baker

[57] ABSTRACT

In a radiation image recording system in which a stimulable phosphor sheet is exposed to an imagewise radiation to record a latent image of a radiation image in the form of stored energy of radiation, the stimulable phosphor sheet is then exposed to stimulating rays to emit light according to the stored energy of radiation, and the emitted light is detected to obtain an image signal, light spontaneously emitted from the stimulable phosphor sheet upon exposure to the imagewise radiation is detected. Then, image processing data such as the maximum value, the minimum value and/or the average value of the stored energy level over the entire area of the image are calculated based on the amount of the light, and is recorded on the stimulable phosphor sheet or the cassette thereof. The image processing data are used for processing the image signal when recording a final image on a recording material.

14 Claims, 6 Drawing Figures

METHOD OF AND APPARATUS FOR RECORDING IMAGE PROCESSING DATA IN RADIATION IMAGE RECORDING SYSTEM

BACKGROUND OF THE INVENTION

1. Field of the Invention

This invention relates to a radiation image recording system in which a stimulable phosphor sheet is exposed to a radiation transmitted through an object to store the energy of the radiation and record a latent image of a radiation image in the form of stored energy of radiation, the stimulable phosphor sheet is then exposed to stimulating rays to emit light according to the stored energy of radiation, the emitted light is detected to obtain an image signal, and the obtained image signal is processed to improve the quality of a final visualized image of the object upon formation of the final image according to image processing data obtained by analyzing the image signal, and more particularly to an improved method of recording the image processing data for use in processing the image signal when recording the final image and an apparatus for carrying out the method.

2. Description of the Prior Art

There has been known a radiation image recording system in which a stimulable phosphor sheet is exposed to an imagewise radiation to store the energy of the radiation and record a latent image of a radiation image in the form of stored energy of radiation, and the stimulable phosphor sheet carrying the radiation latent image is exposed to stimulating rays to emit light according to the stored energy as disclosed in, for example, U.S. Pat. No. 3,859,527.

In the radiation image recording system, a finally read out image is recorded on a photosensitive material like a photographic film or displayed on a cathode ray tube (CRT). The image recorded on the photosensitive material or displayed on the CRT (which will be referred to as "final image" hereinbelow) should have high image quality and particularly should have high diagnostic efficiency and accuracy when the final image is a radiograph used for medical diagnosis. In order to obtain a desirable final image the read out image should preferably be electrically processed when recording the final image. For example, the stimulable phosphor carrying the radiation latent image is exposed to a laser beam or other stimulating rays to emit light according to the stored energy and the emitted light is detected to read out image information. The read out image information is converted to an electric signal and the obtained electric signal is analyzed to obtain image processing data such as information whether a low key or a high key should be used when recording the final image with the electric image signal, or whether the contrast of the radiation image is high or low. The analysis is carried out by calculating the maximum value, the minimum value and/or the average value, etc. from the electric image signal. The brightness, the contrast and the like of the final image may be controlled based on the result of the above analysis.

However, in order to carry out the above method when recording the final image, the whole information of the read out image must once be stored or memorized prior to said analysis. This inherently requires a memory unit having a large capacity. For example, the memory unit must be able to memorize a huge amount of information of $3.6 \times 10^7$ bits assuming that an image of 30 cm×30 cm is detected through apertures of $50\mu + 50\mu$. This prohibitively increases the manufacturing cost of the apparatus.

Further, this method will involve a substantial time lag, since said huge amount of information must be read out and the image analysis must be conducted using the read out information when recording the final image.

The inventors of the present invention have found that when a stimulable phosphor is exposed to a radiation, the stimulable phosphor stores a part of the energy of the radiation absorbed thereby and simultaneously discharges the rest of the energy as a spontaneous emission of light, and that the amount of the light momentarily emitted from the stimulable phosphor is proportional to the amount of the energy stored therein. Thus, information of the characteristics of the radiation image recorded on the stimulable phosphor in the form of stored energy of radiation can be obtained by detecting the spontaneous emitted light. The inventors have proposed a method of recording a final image in which image processing data are obtained through a calculation involving the information of the image characteristics obtained in the above manner and the image processing data are used for processing the electric image signal when recording the final image. (See U.S. patent application Ser. No. 80,310 now U.S. Pat. No. 4,284,889)

The information of the image characteristics can also be obtained simultaneously with recording the radiation latent image on the stimulable phosphor by exposing a detecting phosphor means like a phosphor plate or a number of phosphor members disposed behind the stimulable phosphor over the entire area thereof to the radiation transmitted through the object and and causing the phosphor to emit light. In this case, the material of the detecting phosphor means can be selected freely, and accordingly, an effective detection can be conducted by using a phosphor which can emit light of high luminance. The amount of the light emitted from the detecting phosphor means is also proportional to the amount of the energy stored in the stimulable phosphor. Therefore, the information of the image characteristics can be obtained by detecting the amount of the light emitted from the additional phosphor.

Each of the obtained image processing data must be accurately identified to correspond to each of the stimulable phosphor sheets for the data. This can be done by storing the obtained image processing data in a memory unit of a computer together with the serial number of the stimulable phosphor sheet corresponding thereto or by recording the image processing data on a recording medium together with the reference numeral of the corresponding stimulable phosphor sheet. However, these methods are disadvantageous in that the reference numeral or the serial number must be recorded on each of the stimulable phosphor sheets or the cassettes containing therein the phosphor sheet, which is troublesome. Further, the reference numerals or the serial numbers must be referred to when inputting the image processing data to the memory unit of the computer, during which miscorrespondence between the specific image processing data and the stimulable phosphor sheet is apt to occur.

SUMMARY OF THE INVENTION

In view of the foregoing observation and the description, the primary object of the present invention is to provide a method a recording image processing data on the corresponding stimulable phosphor sheet or the cassette containing therein the stimulable phosphor sheet with the recording of a radiation image on the stimulable phosphor sheet.

Another object of the present invention is to provide an apparatus for carrying out the method of recording the image processing data.

In the method of the present invention, light emitted from a stimulable phosphor or a detecting phosphor means provided behind the stimulable phosphor upon exposure of the stimulable phosphor to an imagewise radiation to record thereon a radiation latent image in the form of stored energy of radiation is photoelectrically detected over the entire area of the image to obtain information of the image characteristics. The obtained information is introduced into an arithmetic and logical unit to calculate various image processing data based on the information. The calculated image processing data is recorded on the stimulable phosphor or on a portion of a cassette containing the stimulable phosphor therein.

In one aspect of the present invention, an apparatus for carrying out the method of the present invention comprises, means for supporting a stimulable phosphor sheet or a cassette containing therein the stimulable phosphor sheet, an array of a number of photodetectors disposed behind the stimulable phosphor sheet over the entire area thereof for detecting light spontaneously emitted therefrom upon exposure of the stimulable phosphor sheet to an imagewise radiation transmitted through an object, an arithmetic and logical unit connected to the output of the photodetectors for conducting an operation for calculating desired image processing data based on the outputs of the photodetectors, and a data recording means for recording the obtained image processing data on the stimulable phosphor sheet or the cassette containing the phosphor sheet therein based on the output of the arithmetic and logical unit.

In another aspect of the present invention, an apparatus for carrying out the method of the present invention comprises, means for supporting a stimulable phosphor sheet, detecting phosphor means which is disposed behind the stimulable phosphor sheet over the entire area thereof and upon exposure of the stimulable phosphor sheet to an imagewise radiation transmitted through an object receives the same radiation and is caused to emit light thereby, an array of a number of photodetectors for detecting the light emitted from the detecting phosphor means arranged over the entire area of the stimulable phosphor sheet, an arithmetic and logical unit connected to the output of the photodetectors for conducting an operation for calculating desired image processing data based on the outputs of the photodetectors, and a data recording means for recording the obtained image processing data on the stimulable phosphor sheet or the cassette containing the phosphor sheet therein based on the output of the arithmetic and logical units.

The image processing data recorded on the stimulable phosphor sheet or the cassette containing the phosphor sheet in accordance with the present invention is utilized, when reading out the image information by exposing the stimulable phosphor sheet to stimulating rays, for processing images as disclosed in Japanese patent application No 53(1978)-163571, 53(1978)-163573, 54(1979)-23092 and the like, or for controlling the gain of a photo-electric converter such as a photomultiplier for detecting the amount of emitted light to obtain an image of high quality.

As the stimulating rays for stimulating the stimulable phosphor to cause the phosphor to emit light is used a laser beam having high directivity. As the light source for the laser beam is preferred a laser source capable of emitting light having a wavelength within the range of 500 to 800 nm, preferably 600 to 700 nm. For example, a He-Ne laser (633 nm) and a Kr laser (647 nm) can be used. Other light sources can be used if combined with a filter which cuts off the light of the wavelength of less than 500 nm and more than 800 nm.

In the present invention, the stimulable phosphor may be defined as a phosphor which, after exposure to an initial radiation like X-rays, $\alpha$-rays, $\beta$-rays, $\gamma$-rays and ultraviolet rays, emits light of the amount corresponding to the energy of the stored radiation when stimulated optically.

As the stimulable phosphor, a phosphor is preferred which emits light having a wavelength within the range of 300 to 500 nm. One example of this phosphor is rare earth activated alkaline earth metal fluorohalide phosphor, as shown in Japanese unexamined Patent Publication No. 55(1980)-12143 (corresponding to U.S. Patent Application No. 169,954 now abandoned), a phosphor represented by the formula $(Ba_{1-x-y},Mg_x,Ca_y)FX:aEu^{2+}$ wherein X is at least one of Cl and Br, x and y are numbers satisfying $0 < x+y \leq 0.6$ and $xy \neq 0$, and a is a number satisfying $10^{-6} \leq a \leq 5 \times 10^{-2}$. Another example of this phosphor is, as shown in Japanese unexamined Patent Publication No. 55(1980)-12145 (corresponding to U.S. Pat. No. 4,239,968), a phosphor represented by the formula $(Ba_{1-x},M^{II}_x)FX:yA$ wherein $M^{II}$ is at least one of Mg, Ca, Sr, Zn and Cd, X is at least one of Cl, Br and I, A is at least one of Eu, Tb, Ce, Tm, Dy, Pr, Ho, Nd, Yb and Er, x is a number satisfying $0 \leq x \leq 0.6$, and y is a number satisfying $0 \leq y \leq 0.2$. Further, as the stimulable phosphor to be used in this invention, there can be used AnS:Cu,Pb; $BaO.xAl_2O_3$:Eu wherein $0.8 \leq x \leq 10$; and $M^{II}O.xSiO_2$:A wherein $M^{II}$ is Mg, Ca, Sr, Zn, Cd or Ba, A is Ce, Tb, Eu, Tm, Pb, Tl, Bi or Mn, and x is a number satisfying $0.5 \leq x \leq 2.5$, as shown in Japanese unexamined Patent Publication No. 55(1980)-12142 (corresponding to U.S. Pat. No. 4,236,078). Furthermore, as the stimulable phosphor, there can be used LnOX:xA wherein Ln is at least one of La, Y, Gd and Lu, X is at least one of Cl and Br, A is at least one of Ce and Tb, x is a number satisfying $0 < x < 0.1$, as shown in Japanese unexamined Patent Publication No. 55(1980)-12144 (corresponding to above mentioned U.S. Pat. No. 4,236,078). Among the above numerated phosphors, the rare earth activated alkaline earth metal fluorohalide phosphor is the most preferable, among which barium fluorohalides are the most preferable in view of the high intensity of emission of light.

Further, it is desirable to color the phosphor layer of the stimulable phosphor plate made of the above phosphor by use of pigments or dyes to improve the sharpness of the image obtained thereby as disclosed in Japanese Patent Application No. 54(1979)-71604.

The photodetectors for receiving the light spontaneously emitted from the stimulable phosphor when the phosphor is exposed to a radiation are arranged to obtain image information of a predetermined range. For example, a plurality of photodetectors like photodiodes are arranged to form a matrix for receiving light from the whole area of the stimulable phosphor sheet. The number of the photodetectors may be noticeably smaller than that of the photodetectors for reading out the image provided that it is sufficient for detecting the characteristics of the image (e.g. one/1–25 cm$^2$).

As the detecting phosphor means for emitting light when exposed to the radiation transmitted through the object and the stimulable phosphor sheet, an ordinary phosphor rather than stimulable phosphor can be used. It may be in the form of a single phosphor sheet having a size substantially equal to the size of the stimulable phosphor sheet, or a group of a number of small phosphor members arranged in a matrix. In the latter case, the photodetectors are located right behind the small phosphor members.

Said obtained image processing data can be recorded on the stimulable phosphor sheet or the cassette containing it in various ways. For example, the image processing data may be magnetically recorded on a magnetic recording medium on the stimulable phosphor sheet or the cassette by means of a magnetic recording head which converts the output of the arithmetic and logical unit into a magnetic recording signal. Further the image processing data may be optically recorded on the stimulable phosphor sheet directly. For example, the output of the arithmetic and logical unit is inputted to an optical recording device comprising a character displaying element using LEDs and the image processing data are optically recorded on the stimulable phosphor sheet. When optically recording the image processing data on the cassette, the cassette is provided with an optical recording medium or a photosensitive material on the surface thereof. For instance, a photosensitive or thermosensitive material as used in a laser scanning recording system can be employed. Practically, the photosensitive material which does not require a developing process is preferred.

DESCRIPTION OF THE PREFERRED EMBODIMENTS

Figure 1:
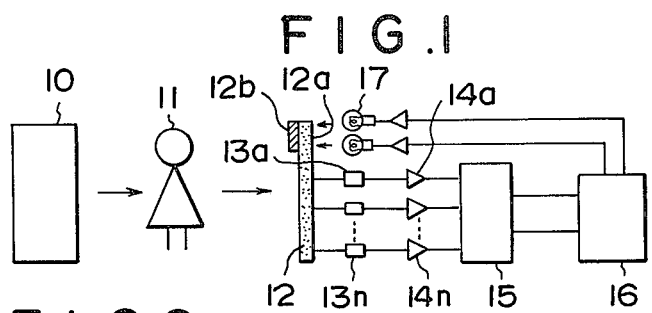
FIG. 1 is a schematic view illustrating an X-ray image recording system employing the present invention.

FIG. 1 is a schematic view illustrating an X-ray image recording system employing the method of the present invention. In FIG. 1, a human body 11 is exposed to X-rays emitted from an X-ray source 10. The X-rays transmitted through the human body 11 impinge upon a stimulable phosphor sheet 12 behind the human body 11. The stimulable phosphor sheet 12 comprises a supporting sheet and a stimulable phosphor layer [e.g. {ZnS(0.8), CaS(0.2)}:Ag, BaP:SiO$_2$, BaFBr:Eu, BaFCl:Eu] coated thereon together with a binder. The stimulable phosphor stores a part of the energy of the X-rays to record an X-ray transmission image of the human body 11 in the form of stored energy of X-rays. At the same time the stimulable phosphor sheet 12 discharges the rest of the absorbed energy of the X-ray as spontaneous emission of light. The light spontaneously emitted from the stimulable phosphor sheet 12 is detected by a plurality of photodetectors 13a, 13b . . . 13n disposed behind the stimulable phosphor sheet 12. The photodetectors may be photomultipliers, silicon detectors, solar cells, or photodiodes arranged in two-dimensions.

The outputs of the photodetectors 13a, 13b . . . 13n are amplified by amplifiers 14a . . . 14n and then fed to an arithmetic and logical unit 15 for calculating the maximum value, the minimum value and/or the average value to obtain the maximum brightness, the minimum brightness and/or the average brightness. If it is sufficient to detect only the average brightness as the image processing data, it is possible to use only one photodetector. As described above, the amount of light spontaneously emitted from the stimulable phosphor sheet 12 is accurately proportional to the amount of the energy stored therein. The maximum, minimum and/or average amount of the light spontaneously emitted from the stimulable phosphor sheet 12 can easily be converted to signals representing the maximum, minimum and/or average amount of the stored energy according to a predetermined relationship which depends on the kind of phosphor used and the structure of the read out device. This conversion is conducted by a converting means 16 and the result of the conversion is recorded as image processing data on a portion 12a of the stimulable phosphor sheet 12 in the above described manner. The portion 12a is shielded from the X-rays by a shield plate 12b to prevent the portion 12a from being exposed to the X-rays.

When recording the image processing data on the portion 12a, an ultraviolet ray source 17 is used. The image processing data may be recorded either in a digital form or in an analog form.

Figure 2:
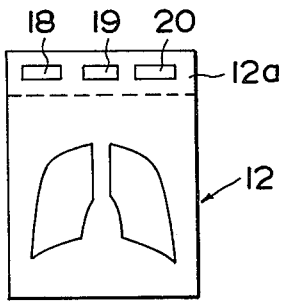
FIGS. 2 and 4 are views respectively showing examples of the stimulable phosphor sheets provided with different recording media for recording the image processing data in accordance with the present invention.

An example of the form of the record is shown in FIG. 2. In this example, the characteristics of the X-ray image such as the maximum value, the minimum value and/or the average value recorded on the stimulable phosphor sheet 12 by the initial exposure to the X-rays are converted into ultraviolet rays having intensities corresponding to the maximum, minimum and/or average values, respectively. Recording spaces 18, 19 and 20 provided within the portion 12a are exposed to the ultraviolet rays to record the values, respectively. Of course, the portion 12a should be shielded from the X-rays.

Figure 3:
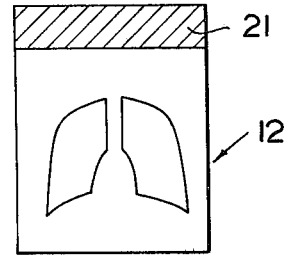

In another example shown in FIG. 3, a magnetic recording strip 21 is attached to the stimulable phosphor sheet 12 in an area which would not obstruct the X-rays for recording the image. The image processing data is recorded magnetically on the magnetic recording strip 21. The magnetic recording may be carried out by use of a magnetic recording head which is moved along the magnetic recording strip 21 or by use of a plurality of magnetic recording heads arranged along the magnetic recording strip 21.

Figure 4:
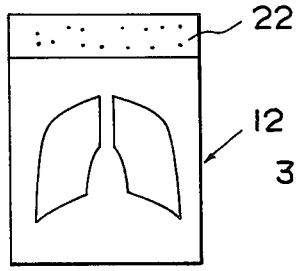

Further, as shown in FIG. 4, the image processing data may be optically recorded on a photochromic recording layer 22 provided on the stimulable phosphor sheet 12 in an area which would not obstruct the X-rays for recording the image.

In any of the above methods of recording, the record can be erased to permit repeated use of the stimulable phosphor sheet 12. When the stimulable phosphor sheet 12 may not be repeatedly used, then diazo photosensitive material and electrophotographic material may be used. Further the image processing data can be mechanically recorded by means of, for example, an ink jet recording device or a perforator.

Further, various kinds of information other than the image characteristics such as the date of radiation exposure, an identification of the object and radiation exposure conditions may be recorded by means of another input device.

When the stimulable phosphor sheet 12 is contained in a cassette, the image processing data may be recorded on the cassette. In such a case, the cassette is provided with a magnetic recording strip or an optical recording medium such as a photochromic material layer, a photographic material layer, a diazo photosensitive material layer or an electrophotographic material layer to magnetically or optically record the image processing data. When mechanically recording the image processing data on the cassette, a portion suitable for mechanical recording is provided on the cassette.

Figure 5:
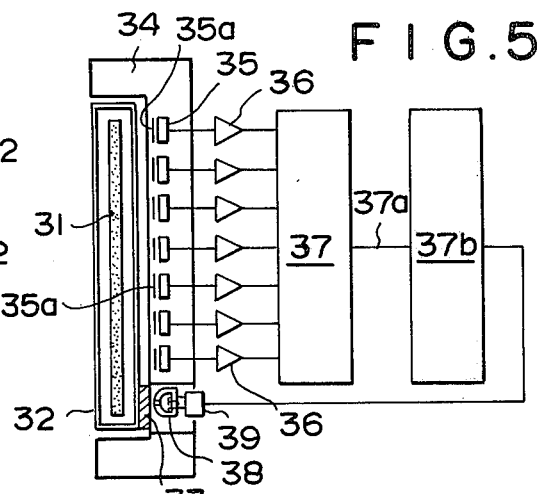
FIG. 5 is a schematic view illustrating an embodiment of an apparatus for carrying out the method of the present invention.

FIG. 5 shows an embodiment of an apparatus for carrying out the method of the present invention in which the image processing data are obtained by detection of the light emitted from detecting phosphor elements 35a provided behind the stimulable phosphor sheet 31, and is magnetically recorded on a cassette 32 containing the stimulable phosphor sheet 31. In FIG. 5, a stimulable phosphor sheet 31 is contained in a cassette 32. A magnetic recording tape 33 is attached to the cassette 32 on the rear surface thereof adjacent to the lower end. The cassette 32 is supported on a cassette holder 34. The cassette holder 34 also supports a number of phosphor elements 35a arranged in a matrix disposed behind the cassette 32 over the entire area thereof and a plurality of photodetectors 35 disposed right behind the phosphor elements 35a, respectively. The photodetectors 35 are connected to an arithmetic and logical unit 37 through amplifiers 36. The output 37a of the arithmetic and logical unit 37 is connected through a signal converting means 37b to a recording circuit 39. The recording circuit 39 gives a magnetic recording signal to a magnetic recording head 38 disposed within the cassette holder 34. The magnetic recording head 38 is moved along the magnetic recording tape 33 by means of a driving means (not shown). The arithmetic and logical unit 37 receives the outputs of the photodetectors 35 through the amplifiers 36 and calculates, for example, the maximum, minimum and/or average values thereof as the image processing data. The calculated values are recorded on the magnetic recording tape 33 by means of the magnetic recording head 38. The image processing data thus recorded always accompany the cassette 32 and are easily used for processing the image read out from the stimulable phosphor sheet 31 when recording the final image.

Figure 6:
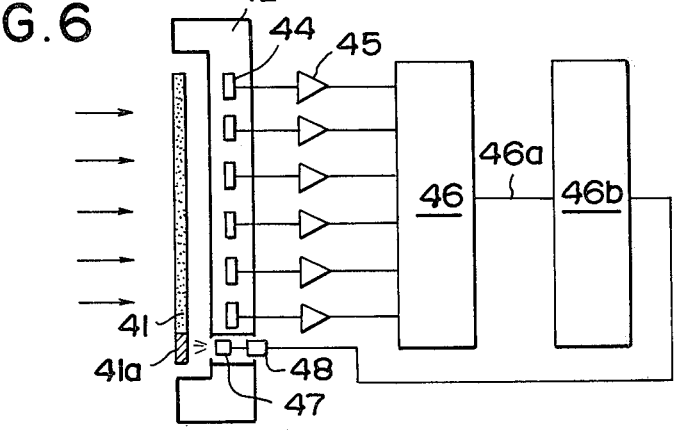
FIG. 6 is a schematic view illustrating another embodiment of an apparatus for carrying out the method of the present invention.

FIG. 6 shows another embodiment of an apparatus for carrying out the method of the present invention. In this embodiment, the image processing data are obtained through detection of light spontaneously emitted from the stimulable phosphor sheet 41 and are recorded on the stimulable phosphor sheet 41. The stimulable phosphor sheet 41 is supported by a sheet holder 42. The sheet holder 42 also supports a number of photodetectors 44 arranged behind the rear surface of the stimulable phosphor sheet 41. The photodetectors 44 are connected through amplifiers 45 to an arithmetic and logical unit 46. The output 46a thereof is connected through a signal converting means 46b to a driving circuit 48 for operating a light emitting character recording element 47 comprising LEDs disposed within the lower part of the sheet holder 42. Those LEDs which emit red light are used. A portion 41a of the stimulable phosphor sheet 41 opposed to the character recording element 47 is uniformly exposed to X-rays or ultraviolet rays in advance upon exposure of the stimulable phosphor sheet 41 to the imagewise X-rays, whereby the energy of X-rays or ultraviolet rays is uniformly stored over the entire area of the portion 41a. When the portion 41a is exposed to red light, the energy stored in the exposed part of the portion 41a is discharged. Thus, desired characters can be recorded on the portion 41a in a negative form by operating the character recording element 47 after uniformly exposing the portion 41a to the X-rays. The character recording element 47 may comprise, for example, a plurality of figure displaying devices including seven segments of light emitting diodes and be held in close contact with the rear surface of the portion 41a of the stimulable phosphor sheet 41. The image processing data thus recorded on the stimulable phosphor sheet 41 at the portion 41a are read out when the image recorded on the stimulable phosphor sheet 41 is read out and are inputted to a recording means for recording the final image by use of the image processing data.

The photodetectors 13, 35 or 44 may be arranged in parallel rows or radial rows. Further, they may be arranged in a matrix.

We claim:

1. In a radiation image recording method in which a stimulable phosphor is exposed to an imagewise radiation transmitted through an object to store the energy of the radiation and record a latent image of a radiation image, the stimulable phosphor is then exposed to stimulating rays to read out the recorded image in the form of the stored energy of radiation thereon, light spontaneously emitted from the stimulable phosphor upon exposure of the stimulable phosphor to the imagewise radiation is photoelectrically detected over the entire area of the image to obtain information of the image, and the obtained image information is fed to an arithmetic and logical unit to calculate various desired image processing data, the improvement comprising the step of recording the calculated image processing data on the stimulable phosphor.

2. In a radiation image recording method in which a stimulable phosphor is exposed to an imagewise radiation transmitted through an object to store the energy of the radiation and record a latent image of a radiation image, the stimulable phosphor is then exposed to stimulating rays to read-out the recorded image in the form of the stored energy of radiation thereon, light spontaneously emitted from the stimulable phosphor upon exposure of the stimulable phosphor to the imagewise radiation as photoelectrically detected over the entire area of the image to obtain information of the image, and the obtained image is fed to an arithmetic and logical unit to calculate various desired image processing data, the improvement comprising the step of recording the calculated image processing data on a cassette containing the stimulable phosphor therein.

3. A method as defined in claims 1 or 2 wherein said image processing data includes a value corresponding to at least one of the maximum value, the minimum value and the average value of the amount of the light emitted from said stimulating phosphor or said detecting phosphor means.

4. A method as in claim 1 or 2 including detecting the light emitted from the stimulable phosphor means by detecting phosphor means disposed along the stimulable phosphor, the light emitted from the detecting phosphor means being detected during said photoelectrically detecting step.

5. An apparatus for recording image processing data in a radiation image recording system, said apparatus comprising,
   means for supporting a stimulable phosphor sheet,
   an array of a number of photodetectors disposed behind the stimulable phosphor sheet over the entire area thereof for detecting light spontaneously emitted therefrom upon exposure of the stimulable phosphor sheet to an imagewise radiation transmitted through an object,
   an arithmetic and logical unit connected to the output of the photodetectors for calculating desired image processing data based on the outputs of the photodetectors, and
   a data recording means for recording the obtained image processing data on the stimulable phosphor sheet based on the output of the arithmetic and logical unit.

6. An apparatus as defined in claim 5 wherein said data recording means is a magnetic recording means which magnetically records the image processing data on a magnetic recording medium provided on a portion of the stimulable phosphor sheet.

7. An apparatus as defined in claim 5 wherein said data recording means is a light emitting device and said image processing data are optically recorded on an optical recording medium provided on said stimulable phosphor sheet directly.

8. An apparatus for recording image processing data in a radiation image recording system, said apparatus comprising,
   means for supporting a stimulable phosphor sheet,
   detecting phosphor means which is disposed behind the stimulable phosphor sheet over the entire area thereof and upon exposure of the stimulable phosphor sheet to an imagewise radiation transmitted through an object receives the same radiation and is caused to emit light thereby,
   an array of a number of photodetectors for detecting the light emitted from the detecting phosphor means arranged over the entire area of the stimulable sheet,
   an arithmetic and logical unit connected to the output of the photodetectors for calculating desired image processing data based on the outputs of the photodetectors, and
   a data recording means for recording the obtained image processing data on the stimulable phosphor sheet based on the output of the arithmetic and logical unit.

9. An apparatus for recording image processing data in a radiation image recording system, said apparatus comprising,
   a cassette containing therein a stimulable phosphor sheet,
   detecting phosphor means which is disposed behind the stimulable phosphor sheet over the entire area thereof and upon exposure of the stimulable phosphor sheet to an imagewise radiation transmitted through an object receives the same radiation and is caused to emit light thereby,
   an array of a number of photodetectors for detecting the light emitted from the detecting phosphor means arranged over the entire area of the stimulable sheet,
   an arithmetic and logical unit connected to the output of the photodetectors for calculating desired image processing data based on the outputs of the photodetectors, and
   a data recording means for recording the obtained image processing data on the cassette containing the phosphor sheet therein based on the output of the arithmetic and logical unit.

10. An apparatus as defined in claims 8 or 9 wherein said detecting phosphor means is a single phosphor sheet extending over the entire area of the stimulable phosphor sheet.

11. An apparatus as defined in claims 8 or 9 wherein said detecting phosphor means is a plurality of phosphor elements arranged over the entire area of said stimulable phosphor sheet and said photodetectors are disposed right behind the phosphor elements, respectively.

12. An apparatus for recording image processing data in a radiation image recording system, said apparatus comprising,
    a cassette containing a stimulable phosphor sheet therein,
    an array of a number of photodetectors disposed behind the stimulable phosphor sheet over the entire area thereof for detecting light spontaneously emitted therefrom upon exposure of the stimulable phosphor sheet to an imagewise radiation transmitted through an object,
    an arithmetic and logical unit connected to the output of the photodetectors for calculating desired image processing data based on the outputs of the photodetectors, and
    a data recording means for recording the obtained image processing data on the cassette containing the phosphor sheet therein based on the output of the arithmetic and logical unit.

13. An apparatus as defined in claim 12 wherein said data recording means is a magnetic recording means which magnetically records the image processing data on a magnetic recording medium provided on the cassette containing said stimulable phosphor sheet.

14. An apparatus as defined in claim 12 wherein said data recording means is a light emitting device and said image processing data are optically recorded on an optical recording medium provided on said cassette.

* * * * *